United States Patent [19]

Scordato

[11] 4,454,752
[45] Jun. 19, 1984

[54] TEST CIRCUIT FOR USE IN COAGULATION INSTRUMENT

[75] Inventor: Richard E. Scordato, Scarsdale, N.Y.

[73] Assignee: Medical Laboratory Automation, Inc., Mount Vernon, N.Y.

[21] Appl. No.: 390,679

[22] Filed: Jun. 21, 1982

[51] Int. Cl.³ ............................................. G01N 33/48
[52] U.S. Cl. ....................................... 73/64.1; 73/1 R; 356/39; 422/73; 436/69
[58] Field of Search ...................... 73/64.1, 432 SD, 5, 73/1 R; 356/39; 364/578; 422/73; 436/69

[56] References Cited

U.S. PATENT DOCUMENTS 3,658,480 4/1972 Kane et al. ...................... 73/64.1 X Primary Examiner—S. Clement Swisher
Assistant Examiner—Joseph W. Roskos
Attorney, Agent, or Firm—William P. Keegan

[57] ABSTRACT

In a photometric coagulation instrument a synthetic clot signal is generated so that the operation of the instrument can be checked without the need to measure the actual clotting time of a control plasma sample.

13 Claims, 5 Drawing Figures

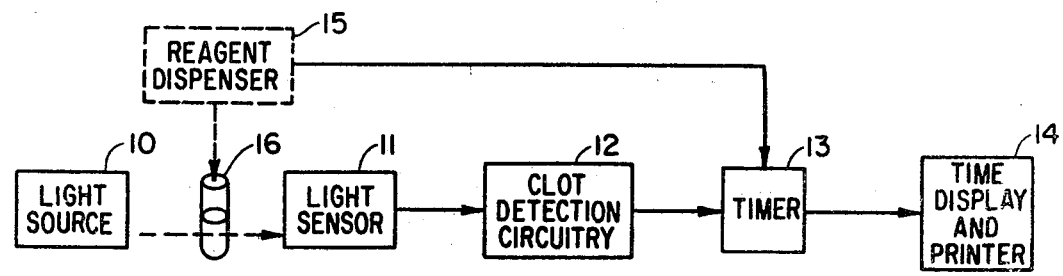
FIG.1
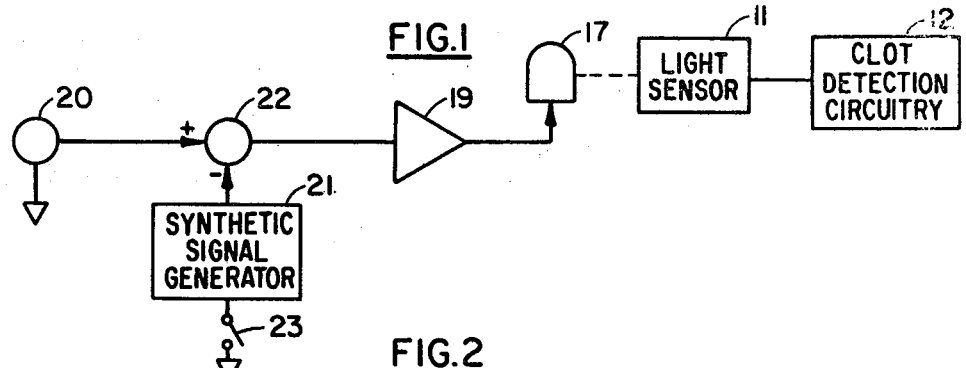
FIG.2
FIG.3
FIG.4
FIG.5

TEST CIRCUIT FOR USE IN COAGULATION INSTRUMENT

FIELD OF THE INVENTION

The invention relates to instruments that measure clotting time of blood or blood components, and more particularly to such instruments as determine the prothrombin time or the activated partial thromboplastin time of plasma samples.

BACKGROUND OF THE INVENTION

For many years coagulation instruments have been provided to measure the clotting time of human plasma through the use of photometric techniques. In such instruments, a light beam is directed through a plasma sample to which a suitable reagent has been added. The light passing through the sample is sensed by a light sensitive element or photocell, and as the plasma goes through the clotting process and becomes less translucent, the light falling on the photocell decreases. Thus, an electrical signal from the photocell can be processed by electronic circuitry to provide an accepted measure of clotting time. In instruments that are available in the marketplace, the electronic circuitry generally includes means that provide a first or a second derivative signal of the optical density signal obtained at the photocell. At a point determinative of clot formation, the derivative signal will stop a timer that had been started when the reagent was added to the plasma sample to initiate the clotting process. The timer output is taken as a measure of the clotting time of the plasma. Normal clotting time for prothrombin time measurements is about 12 seconds while for activated partial thromboplastin time measurements a normal clotting time will be between 20 and 35 seconds.

A modern coagulation instrument is a complex device comprising many subsystems that enable automation of plasma coagulation tests such as those referred to above. For example, there are cooling elements that maintain plasma samples and reagents at desired storage temperatures, i.e., 8° C., and heating elements that raise the temperatures of the plasma and the reagents to 37° C. when they are mixed to initiate clot formation. Of course, there is the electronic circuitry that responds to the photocell signal to detect the formation of a clot.

When erroneous results are obtained from the instrument, as indicated by clotting times that materially deviate from the expected clotting times obtained on standardized control plasma, it becomes a significant problem for the technician using the instrument to determine which element or component of the instrument is faulty or malfunctioning, if indeed the failure is due to the instrument itself. Erroneous results can also result, for example, from the use of substandard reagents that may have deteriorated during storage, but it is the initial tendency to blame the instrument for the error. Certain operational characteristics of the instrument, such as the temperature condition of a component or reagent volumes delivered by pumping mechanisms, can be checked by conventional means, but there is no convenient way for the technician to check that the electronic circuitry is performing as it should.

BRIEF DESCRIPTION OF THE INVENTION

It is, therefore, the object of the invention to provide means whereby a technician may check the coagulation instrument to ascertain that the clot detection electronic circuits are functioning satisfactorily.

Another object of the invention is to provide circuit means that generate a signal which is similar to the signal generated by the formation of a clot in a plasma sample.

Still another object of the invention is to provide means for checking the clot detection circuits of the instrument without the need to run coagulation tests using standard control reagents and plasma.

Yet another object of the invention is to provide an improved coagulation instrument that inspires confidence in its reliability by permitting the clot detection circuitry to be checked readily so as to encourage checking of the instrument before each run of tests using patients' plasma samples.

It is, therefore, the object of the invention to provide an improved coagulation instrument.

In carrying out the invention, there is provided a signal generator that provides a signal which, at the photocell of the instrument, causes the output circuit from the photocell to the clot detection circuitry to carry a signal that is similar to one which the photocell would generate in response to a clot being formed in a plasma sample placed in the light path to the photocell. This clot simulating signal can be produced either by decreasing the light falling on the photocell as by decreasing the light output of the light source, or by directly modifying the signal output from the photocell. There is also provided means for starting the instrument timer when the synthetic clot signal is applied to the circuitry so that the instrument can print out a "clot" time. If the clot time for the synthetic clot signal is of the proper value, the technician using the instrument will know that the instrument is performing satisfactorily.

DESCRIPTION OF THE DRAWING

FIG. 1 is a simplified schematic block diagram of a photometric clot timing instrument;

FIG. 2 is a schematic circuit diagram showing where a synthetic clot signal may be introduced into the circuitry of a photometric clot timing instrument;

FIG. 3 is a circuit diagram similar to FIG. 2 showing another circuit arrangement;

FIG. 4 is a series of curves representing various signals that may be produced in a photometric clot timing instrument; and FIG. 5 is a schematic circuit diagram of a circuit for generating a signal simulating a clot signal.

DETAILED DESCRIPTION OF THE INVENTION

A preferred embodiment of the invention is hereinafter disclosed.

In FIG. 1 there is shown a simplified block diagram of a coagulation instrument comprising a light source 10, a light sensor 11, optical density and clot detection circuitry 12, a timer 13, and a time display unit and printer 14. A reagent dispensing mechanism 15 is provided to add the proper reagent for running a prothrombin time (PT) or an activated partial thromboplastin time (APTT) test to a plasma sample 16 located in the light path between light source 10 and light sensor 11. At the instant the reagent is added to the plasma to initiate the clotting process, clot timer 13 is started. When the clot formation is detected by circuitry 12, the timer is stopped and the elapsed time is displayed and printed on a suitable record in printer 14.

Commercial instruments generally provide a clot time that is determined by the first derivative or the second derivative signal of the optical density signal measured by the light sensor 11. Of course, sophisticated circuits, not shown and not pertinent to the present invention, are provided to enhance the quality of the signal as it is transmitted through the circuitry of the instrument. This is done to enable the onset of a clot to be more readily and consistently detectable.

As a clot forms in plasma sample 16 and the sample grows less translucent, the light from source 10 falling on light sensor 11 gets less and less. In the absence of an actual clot forming sample in the light path, clot formation can be simulated by decreasing the light output from light source 10. A circuit for simulating the formation of a clot by decreasing the light output from a light source is illustrated in FIG. 2 wherein the light source 10 comprises a lamp 17 powered by a constant voltage source 20 operating through an amplifier/driver 19. The lamp directs light to the light sensor 11 which in turn generates a signal that is transmitted to the optical density and clot detection circuitry 12. According to the present invention, a synthetic clot signal generator 21 provides a signal to the summing junction 22 where the signal is subtracted from the voltage source signal. A switching mechanism 23 is provided to initiate operation of the synthetic clot signal generator 21. It should be clear that as the synthetic clot signal of increasing magnitude is subtracted from the voltage source signal, the voltage applied to lamp 17 decreases and the light from lamp 17 falling on light sensor 11 decreases as would be the case if a clot were forming in the light path between lamp 17 and sensor 11. If lamp 17 is an incandescent lamp, the signal from generator 21 has to compensate for the fact that the output of light from the lamp as a function of the voltage applied to it is highly non-linear. However, this problem of non-linearity is obviated if the lamp is a light emitting diode since the light output therefrom is linear as a function of the applied voltage. Also, since coagulation instruments may provide means for changing the light intensity level of the lamps to compensate for plasma of different translucensies, the clot signal generator 21 would have to provide a signal that is correspondingly adjusted.

A second embodiment of the invention is shown in FIG. 3 wherein the signal from the synthetic clot signal generator 21 is added, in summing junction 24, to the output signal from light sensor 11. In this case, a constant voltage is applied to lamp 17 thus obviating the need for the synthetic clot signal generator to compensate for the non-linearity of an incandescent lamp as would be the case in a FIG. 2 embodiment when an incandescent lamp serves as the light source. The FIG. 3 embodiment also employs switching means 23 to initiate testing of the instrument.

In a coagulation instrument of the type schematically illustrated in FIG. 1, the light sensor 11 will typically provide an optical density signal OD such as shown in the FIG. 4 curve marked OD. The optical density and clot detection circuitry 12 will, at certain points therein, have signals derived from the OD signal such as the first derivative signal OD' and, if a second derivative signal is used in the clot detection circuitry, a second derivative signal OD". The signal representations are shown as a voltage plotted on a time base.

The coagulation instrument will generally interpret some point along the increasing portion of the OD curve, e.g., from point 30 to point 31 as the start of clot formation.

Various techniques are used, but almost all are based upon taking one or two derivatives and comparing these values to a reference. When the reference is exceeded, the clot is detected For purposes of the present disclosure, the synthetic clot signal generator will be described for an instrument that interprets clot formation as starting at point 30 of the OD curve. Such an instrument may provide an OD' or an OD" or a higher derivative signal to indicate the onset of clot formation at point 30. The higher the derivative signal the more abrupt or steeper will be the signal and the easier it will be for the electronics to respond to the signal crossing a threshold level, e.g., voltage level 33 (FIG. 4), and fix the time of clot formation. It is clear from FIG. 4 that it would be easier to electronically sense when the OD" signal crosses threshold level 33 than when an OD' signal crosses the same threshold.

Since only the lower portion of the rise in the OD signal, that is, from point 30 to point 32, need be simulated, synthetic clot signal generator 21 need only produce a signal having a similar waveform. A parabolic or second order waveform conforms very well with the shape of the initial rise of the OD signal. Attention is now directed to FIG. 5 in which the parabolic signal generating elements of synthetic clot signal generator 21 are shown. The circuit is built around operational amplifiers 34 and 35, the circuits for which type components are well known to those skilled in the electronic arts. The reference voltage source 36 is applied to amplifier 34 which integrates the constant voltage and provides an output voltage that is linearly increasing with time. Hence, amplifier 34 may be referred to as a first integrator. The output of amplifier 34 will then be integrated by the second operational amplifier 35 which will then provide a voltage output that increases as a function of time squared. Thus, the output of amplifier 35 provides a second order signal having a parabolic waveform which simulates the waveform of an OD signal generated by a clot forming in a plasma sample.

Switches 40 and 41 will be closed before the test using the synthetic clot signal is performed. When closed, these switches serve to discharge capacitors 42 and 43, respectively, so that the output at terminal 44 is zero volts. Timer 45 provides a time interval that corresponds to the time period before the onset of clot formation. In other words, a time interval is provided that corresponds to the time before point 30 on the OD curve of FIG. 4 when the OD curve is flat.

It is to be noted that normal clot times as obtained from control plasma and control reagents are known to the technician using the coagulation instrument.

The operating sequence is that when the confidence test is called for, switch 23 will be closed and timers 13 and 45 started. At the end of the time interval provided by timer 45, an output signal will be produced to open switches 40 and 41. The voltage output of amplifier 35 will then be a function of time squared. In other words, after the initial interval provided by timer 45 a parabolic waveform synthetic clot signal simulating the rising lower portion of an OD curve, i.e., from point 30 to point 32 (FIG. 4), will be produced at terminal 44 and applied to the summing junction 22 or 24. Therefore, the coagulation instrument will print out a clot time just as if a control plasma sample were being analyzed. The clot time resulting from the imposition of the synthetic clot signal to the clot detection circuitry should be a known value which is the same each time the confidence circuit is operated. If it is, the technician will known that the electronic circuitry of the instrument is working satisfactorily.

At the expiration of a further period of time, timer 45 produces a signal to cause switches 40 and 41 to close thus resetting the synthetic clot signal generator 21 to its standby or initial condition preparatory to the performance of another confidence test.

It is to be understood that other circuits may be employed to simulate a parabolic waveform representing the initial rise of the OD signal resulting from the formation of a clot in a plasma sample. Also, if the clot time is taken at some other point on the OD curve, e.g., the point of inflection of the S-curve between the initial and final OD levels, signals having other waveforms may be generated by the synthetic clot signal generator.

Having thus described the invention, it is clear that many apparently different embodiments or modifications can be conceived that would not depart from the spirit or scope of the invention. Therefore, the foregoing description and the accompanying drawing are to be interpreted in an illustrative sense rather than in a limiting sense.

What is claimed is:

1. A photometric coagulation instrument comprising light source means for directing light through a plasma sample, light sensor means responsive to the light passing through a plasma sample for generating an electrical signal that is a function of the optical density of the plasma sample as a clot forms therein, circuit means responsive to the electrical signal generated by said light sensor means for determining the instant at which the plasma sample is considered to have clotted, timer means responsive to said circuit means for indicating a time measure of the clotting time of the plasma sample, additional circuit means for producing a clot simulating signal that will cause said circuit means to respond as though a plasma sample were placed in the light path between said light source means and said light sensor means, and means for activating said additional circuit means when it is desired to obtain a time measure of clotting time without using a plasma sample and thereby check the operation of said circuit means.

2. A photometric coagulation instrument according to claim 1 wherein said clot simulating signal operates to reduce the light output of said light source means so that said light sensor means responds as though the reduced light falling thereon is the result of a clot forming in a plasma sample.

3. A photometric coagulation instrument according to claim 1 wherein said clot simulating signal operates to cause said circuit means to respond as though an optical density signal from said light sensor means were being applied thereto.

4. A photometric coagulation instrument according to claim 3 wherein said light sensor means generates a constant signal as the result of unimpeded light from said light source means falling thereon, and said clot simulating signal modifies said constant signal whereby the signal to which said circuit means responds simulates an optical density signal resulting from clot formation in a plasma sample placed between said light source means and said light sensor means.

5. A photometric coagulation instrument according to claim claim 1 or 2 or 3 or 4 wherein said additional circuit means includes timer means, and means for generating a signal having a waveshape similar to that of the optical density curve during the period of clot formation.

6. A photometric coagulation instrument according to claim 5 wherein said signal generating means generates a signal that simulates only a portion of the optical density curve during the period of clot formation.

7. A photometric coagulation instrument according to claim 6 wherein said signal generating means generates a signal having a second order waveshape.

8. A photometric coagulation instrument having means for detecting clot formation in a plasma sample and for measuring the time period between the introduction of a reagent into the plasma sample and the onset of clot formation, said instrument comprising generating means for generating a clot simulating signal, and means for switching said signal generating means into the clot formation detecting means so that the instrument will measure a time period resulting from said clot simulating signal.

9. A photometric coagulation instrument according to claim 8 wherein said generating means includes timer means, and a waveform signal generator that simulates the waveform of an optical density signal during clot formation.

10. The method of simulating the optical density signal obtained in a photometric coagulation instrument after a reagent is added to a plasma sample so that the instrument can be checked to see if it measures normal clotting time without the need to test the clotting time of a control plasma, said method comprising the steps of providing a time interval corresponding to the time period that elapses before the onset of the rapid rise in clot density of a plasma sample, and providing at the expiration of said time interval a signal having a waveform corresponding to that of the optical density signal waveform obtained during the rapid rise in the clot density of a plasma sample.

11. The method of checking the operation of the clot detection circuitry of a photometric coagulation instrument which method comprises the steps of generating in a signal generating circuit a synthetic signal that simulates the signal that results during clot formation in a reagent plasma mixture, applying the synthetic signal to the clot detection circuitry of the instrument, and having the instrument indicate the clot time for the synthetic signal.

12. The method of checking the operation of the clot detection circuitry of a photometric coagulation instrument according to claim 11 wherein the synthetic signal simulates the rise in the optical density signal occurring during clot formation, and including the step of delaying the application of the synthetic signal to the clot detection circuitry for an initial time interval.

13. The method of checking the operation of the clot detection circuitry of a photometric coagulation instrument which method comprises the steps of starting the clot timing means of the coagulation instrument, providing an initial time interval, generating a second order synthetic signal that simulates the signal that results from the rise in optical density when a clot forms in a reagent plasma mixture, applying the synthetic signal to the clot detection circuitry of the instrument after the initial time interval, and having the instrument indicate the clot time for the synthetic signal.

* * * * *